United States Patent
Howard

(10) Patent No.: US 7,198,910 B1
(45) Date of Patent: Apr. 3, 2007

(54) NUCLEIC ACID ENCODING MELANIN-CONCENTRATING HORMONE RECEPTOR

(75) Inventor: Andrew D. Howard, Park Ridge, NJ (US)

(73) Assignee: Merck & Co., Inc., Rahway, NJ (US)

( * ) Notice: Subject to any disclaimer, the term of this patent is extended or adjusted under 35 U.S.C. 154(b) by 1033 days.

(21) Appl. No.: 10/031,014

(22) PCT Filed: Jul. 10, 2000

(86) PCT No.: PCT/US00/18733

§ 371 (c)(1),
(2), (4) Date: Jan. 10, 2002

(87) PCT Pub. No.: WO01/05947

PCT Pub. Date: Jan. 25, 2001

Related U.S. Application Data

(60) Provisional application No. 60/143,706, filed on Jul. 14, 1999.

(51) Int. Cl.
C12N 5/10 (2006.01)
C12N 15/11 (2006.01)

(52) U.S. Cl. .................. 435/69.1; 435/320.1; 435/325; 536/23.5

(58) Field of Classification Search ............... 536/23.5; 435/69.1, 320.1, 325
See application file for complete search history.

(56) References Cited

U.S. PATENT DOCUMENTS 6,221,613 B1 * 4/2001 Salon et al. ................. 435/7.1
6,221,616 B1   4/2001 Salon et al.

FOREIGN PATENT DOCUMENTS

| EP | 0 848 060 A2 | 6/1998 |
|---|---|---|
| EP | 0 848 060 A3 | 2/2000 |
| EP | 1 143 000 A1 | 10/2001 |
| WO | WO 96/18651 | 6/1996 |
| WO | WO 99/28492 | 6/1999 |
| WO | WO 00/15793 | 3/2000 |
| WO | WO 00/37113 | 6/2000 |
| WO | WO 00/39279 | 7/2000 |

OTHER PUBLICATIONS

Flier, J.S. et al., Obesity and the hypothalamus: novel peptides for new pathways, Cell, vol. 92, pp. 437-440, 1998.
Knigge, K.M. et al., Melanotropic peptides in the mammalian brain: the melanin-concentrating hormone, Peptides, vol. 17, No. 6, pp. 1063-1073, 1996.
Shimada, M. et al., Mice lacking melanin-concentrating hormone are hypophagic and lean, Nature, vol. 396, pp. 670-677, 1998.
Lakaye, B. et al., Cloning of the rat brain cDNA encoding for the SLC-1 G protein-coupled receptor receptor reveals the presence of an intron in the gene, Biochimica ACTA, vol. 1401, pp. 216-220, 1998.
Kolakowski, I.F., et al., Characterization of a human gene related to genes encoding somatostatin receptors, FEBS Letters, vol. 398, pp. 253-258, 1996.
Qu, D. et al., A role for melanin-concentrating hormone in the central regulation of feeding behaviour, Nature, vol. 380, pp. 243-247, 1996.
Erickson, J.C. et al., Sensitivity to leptin and susceptibility to seizures of mice lacking neuropeptide Y, Nature, vol. 381, pp. 415-418, 1996.
Nahon, J-L., The Melanin-concentrating hormone: from the peptide to the gene, Critical Reviews in Neusobiology, vol. 8, No. 4, pp. 221-262, 1994.

* cited by examiner

*Primary Examiner*—Michael Pak
(74) *Attorney, Agent, or Firm*—Sheldon O. Heber; Jack L. Tribble

(57) ABSTRACT

The present application features two different forms of the human MCH receptor: (1) MCH-R2 and (2) MCH-R3. Such MCH receptors provide a target for achieving a beneficial affect in a patient and facilitate the screening of compounds that modulate MCH receptor activity or expression. Beneficial effects that can be obtained include increasing appetite, decreasing appetite, and reducing stress.

13 Claims, No Drawings

NUCLEIC ACID ENCODING MELANIN-CONCENTRATING HORMONE RECEPTOR

CROSS-REFERENCE TO RELATED APPLICATIONS

The present application claims priority to U.S. Ser. No. 60/143,706, filed Jul. 14, 1999, hereby incorporated by reference herein.

FIELD OF THE INVENTION

The present invention relates to the melanin-concentrating hormone receptor, methods of screening for compounds active at the melanin-concentrating hormone receptor, and methods of using such compounds to achieve a beneficial effect.

BACKGROUND OF THE INVENTION

The references cited herein are not admitted to be prior art to the claimed invention.

Neuropeptides present in the hypothalamus play a major role in mediating the control of body weight. (Flier, et al., 1998. *Cell*, 92, 437–440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi, et al., 1983. *Nature* 305, 321–323.)

In humans two genes encoding MCH have been identified that are expressed in the brain. (Breton, et al., 1993. *Mol. Brain Res.* 18, 297–310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063–1073.)

Pharmacological and genetic evidence suggest that the primary mode of MCH action is to promote feeding (orexigenic). MCH mRNA is up regulated in fasted mice and rats, in the ob/ob mouse (Qu, et al., 1996 *Nature* 380, 243–247), and in mice with targeted disruption in the gene for neuropeptide Y (NPY). (Erickson, et al., 1996. *Nature* 381, 415–418.) Injection of MCH centrally (ICV) stimulates food intake and MCH antagonizes the hypophagic effects seen with α melanocyte stimulating hormone (αMSH). (Qu, et al., 1996. *Nature* 380, 243–247.) MCH deficient mice are lean, hypophagic and have increased metabolic rate. (Shimada, et al., 1998. *Nature* 396, 670–673.)

MCH action is not limited to modulation of food intake as effects on the hypothalamic-pituitary-axis have been reported. (Nahon, 1994. *Critical Rev. in Neurobiol.* 8, 221–262.) MCH may be involved in the body response to stress as MCH can modulate the stress-induced release of CRF from the hypothalamus and ACTH from the pituitary. In addition, MCH neuronal systems may be involved in reproductive or maternal function.

SUMMARY OF THE INVENTION

The present application features two different forms of the human MCH receptor: (1) MCH-R2 and (2) MCH-R3. Such MCH receptors provide a target for achieving a beneficial affect in a patient and facilitate the screening of compounds that modulate MCH receptor activity or expression. Beneficial effects that can be obtained include increasing appetite, decreasing appetite, and reducing stress.

The MCH receptor is a G protein-coupled receptor that transduces an intracellular signal upon MCH binding. The ability of MCH-R1, a shorter length derivative of MCH-R2 and MCH-3 to couple to a $G_i$ protein is illustrated in Example 3, infra.

MCH-R1, MCH-R2 and MCH-R3 are structurally related polypeptides differing by the presence of additional amino acids at the extracellular amino terminus. MCH-R2 has an additional 64 amino acids at its amino terminus compared to MCH-R1. MCH-R3 has an additional 5 amino acids at its amino terminus compared to MCHR-2, and an additional 69 amino acids at its amino terminus compared to MCHR-1. The nucleic acid and amino acid sequences of MCH-R1, MCH-R2, and MCH-R3 are provided for in SEQ. ID. NOs. 1, 2, 3, 4, 5, and 6 (see Example 1 infra). The additional nucleic acids and amino acid regions present in MCH-R3 compared to MCH-R1 is shown in SEQ. ID. NOs. 7 and 8.

Assays measuring MCH receptor activity can employ MCH-R3 or MCH-R2. MCH-R3 is believed to be a naturally occurring MCH receptor since it has the first in frame ATG start codon in the cDNA, while MCH-R1 and MCH-R2 appear to be shorter-length versions of MCH-R3. MCH-R2 ha the best ribosome initiation sequence 5' to the ATG start, 5 of the 9 nts match the optimal sequence: GCC GCC (A or G) CC ATG (SEQ. ID. NO. 10) which could result in MCH-R2 being the highest expressed form of the MCH receptor.

Thus, a first aspect of the present invention describes a purified nucleic acid comprising a nucleotide sequence encoding for at least 5 contiguous amino acids of SEQ. ID. NO. 8. In preferred embodiments the nucleotide sequence encodes for at least 9, at least 18, at least 27 or at least 36 contiguous amino acids of SEQ. ID. NO. 8; the nucleotide sequence encodes for amino acids 1–5 of SEQ. ID. NO. 8; the nucleic acid comprises at least about 18, at least 27, or at least 54 contiguous nucleotides of SEQ. ID. NO. 7; and the nucleic acid comprises or consists of the nucleotide sequence of SEQ. ID. NO. 3, SEQ. ID. NO. 4, SEQ. ID. NO. 5, SEQ. ID. NO. 6, or SEQ. ID. NO. 9.

A "purified nucleic acid" represents at least 5% of the total nucleic acid present in a sample or preparation. In preferred embodiments, the purified nucleic acid represents at least about 50%, at least about 75%, and at least about 95% of the total nucleic acid a sample or preparation. Reference to "purified nucleic acid" does not require that the nucleic acid have undergone any purification and may include, for example, chemically synthesized nucleic acid that has not been purified.

Another aspect of the present invention describes an expression vector able to express a polypeptide comprising at least 5 contiguous amino acids of SEQ. I.D. NO. 8. The expression vector provides one or more regulatory elements functionally coupled to nucleic acid encoding for the polypeptide such that the polypeptide can be transcribed and translated when present in a suitable host. Preferably, the expression vector contains an exogenous promoter transcriptionally coupled to the nucleic acid encoding the polypeptide.

In preferred embodiments the expression vector comprises nucleic acid encoding for at least 9, at least 18, at least 27 or at least 36 contiguous amino acids of SEQ. ID. NO. 8; the expression vector comprises nucleic acid encoding for amino acids 1–5 of SEQ. ID. NO. 8; the expression vector comprises at least about 18, at least 27, or at least 54 contiguous nucleotides of SEQ. ID. NO. 7; and the expression vector comprises the nucleotide sequence of SEQ. ID. NO. 3, SEQ. ID. NO. 5, or SEQ. ID. NO. 9; and the expression vector comprises a nucleotide sequence encoding for polypeptide comprising or consisting of SEQ. ID. 4 or SEQ. ID. NO. 6.

Another aspect of the present invention describes a recombinant cell comprising an expression vector encoding for a polypeptide comprising at least 5 contiguous amino acids of SEQ. ID. NO. 8. The polypeptide can be expressed from the vector when present in the recombinant cell.

Another aspect of the present invention describes a method of preparing a MCH receptor polypeptide comprising the step of growing a recombinant cell containing an expression vector comprising nucleic acid encoding for a MCH receptor polypeptide under conditions suitable for the expression of the MCH receptor polypeptide. Preferably, the expressed MCH receptor polypeptide is purified.

Another aspect of the present invention describes a purified nucleic acid comprising a region of 20 contiguous nucleotides, wherein at least 16 nucleotides present in the region hybridizes to a complementary region of 20 contiguous nucleotides present in SEQ. ID. NO. 7 or the complement thereof. In preferred embodiments the nucleic acid comprises a region of 20 contiguous nucleotides wherein at least 17, at least 18, at least 19, and 20, nucleotides present in the region hybridize to a complementary region of 20 contiguous nucleotides present in SEQ. ID. NO. 7 or the complement thereof.

Another aspect of the present invention describes a polypeptide comprising an amino acid sequence encoding for at least about 9 contiguous amino acids of SEQ. ID. NO. 8, wherein the polypeptide is substantially free of associated proteins. In preferred embodiments the polypeptide comprises at least 18, at least 27, or at least 36 contiguous amino acids of SEQ. ID. NO. 8; and the polypeptide comprises or consists of the amino acid sequence of SEQ. ID. NO. 4 or SEQ. ID. NO. 6.

"Substantially free from associated proteins" means that the polypeptide is at least about 50%, preferably at least about 75%, and more preferably at least about 95% free from other cell membrane proteins which are normally found in a living mammalian cell expressing a MCH receptor.

Another aspect of the present invention describes a method for screening for a compound able to bind a MCH receptor. The method involves the following: (a) expressing a polypeptide comprising MCH-R2, MCH-R3, or a fragment thereof, from recombinant nucleic acid, provided that the fragment comprises at least about 9 contiguous amino acids of SEQ. ID. NO. 8; (b) providing to the polypeptide a test preparation comprising one or more test compounds; and (c) measuring the ability of the test preparation to bind to the polypeptide.

In different embodiments steps (b) and (c) are performed in vitro; steps (a), (b) and (c) are preformed using a whole cell; the polypeptide is expressed from an expression vector; the polypeptide comprises or consists of the amino sequence of SEQ. ID. NO. 6; and the method is performed where said step (b) further comprises the presence of a labeled MCH, and step (c) measures the ability of said test preparation to inhibit binding of said labeled MCH to said polypeptide.

Another aspect of the present invention describes a method for screening for a compound able to modulate MCH receptor activity. The method involves (a) contacting a cell line expressing recombinant nucleic acid encoding for a MCH receptor comprising or consisting of the amino acid sequence of MCH-R2 or MCH-R3 with a test preparation comprising one or more test compounds; and (b) measuring the effect of the test preparation on the activity of the receptor.

In preferred embodiments the MCH receptor comprises or consists of the amino acid sequence of SEQ. ID. NO. 4 or SEQ. ID. NO. 6; and the method further comprises the presence of an MCH receptor agonist.

Another aspect of the present invention describes a method for suppressing appetite comprising the step of administering to a patient an effective amount of means for decreasing MCH receptor expression targeting a nucleic acid region within SEQ. ID. NO. 7. Such "means" are provided for by the materials and structures described herein, and equivalents thereof. Preferred means are antisense nucleic acid and enzymatic nucleic acid. "Targeting a nucleic acid region within SEQ. ID. NO. 7" indicates that the means for decreasing MCH receptor activity contains a region substantially complementary to a segment of SEQ. ID. NO. 7 such that it hybridizes to the target under physiological conditions.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present application describes a longer length version of MCH-R1 which is believed to be a natural MCH receptor (MCH-R3) and a slightly shorter version thereof (MCH-R2). MCH-R2 and MCH-R3 have a variety of different uses including being a target of receptor cloning, a target for receptor identification, a target for the production of antibodies, and a target for receptor modulation. Additional uses include being used in assays to determine the ability of a test preparation to modulate MCH receptor activity and in gene therapy.

Nucleic acid and amino acid sequences corresponding to MCH-R1 have been characterized in the art as encoding for a somatostatin-like receptor (SLC-1). For example, human and rat SLC-1 are described by Lakaye, et al., 1998. *Biochimica et Biophysica ACTA* 1401:216–220 (which is not admitted to be prior art to the claimed invention). Additionally, a receptor characterized as a human somatostatin-like receptor is referenced in International Publication No. WO 96/18651 and Kolakowski, et al., 1996. *FEBS Letters* 398, 253–258, and an apparent splice variant is referenced in European Publication No. EP 0 848 060 A2 and International Publication No. WO 99/28492 (not admitted to be prior art to the claimed document).

A clone expressing the physiological correct receptor facilitates finding useful agonists or antagonists of the human MCH receptor. In contrast, use of a clone expressing a receptor with a physiologically incorrect MET start would lead to the use of an altered receptor protein, the use of which could be less predictive in finding compounds able to modulate MCH receptor activity.

The MCH receptor provides a target to achieve different beneficial effects in a patient. Preferably, MCH receptor activity is modulated to achieve one or more of the following: weight loss, weight gain, treat cancer (e.g., colon or breast), reduce pain, treat diabetes, reduce stress, or teat sexual dysfunction.

Modulation of MCH receptor activity can be achieved by evoking a response at the MCH receptor or by altering a response evoked by an MCH receptor agonist or antagonist. Compounds modulating MCH receptor activity include agonists, antagonists, and allosteric modulators. Generally, MCH receptor antagonists and allosteric modulators negatively affecting activity will be used to achieve weight loss, treat cancer (e.g., colon or breast), reduce pain, reduce stress, and/or teat sexual dysfunction; and MCH receptor agonists and allosteric modulators positively affecting activity will be used to produce a weight gain.

Preferably, MCH receptor activity is modulated to achieve a weight loss or to treat diabetes in a patient. Diabetes mellitus can be treated by modulating MCH receptor activity to achieve, for example, one or both of the following: enhancing glucose tolerance or decreasing insulin resistance.

Excessive body weight is a contributing factor to different diseases, including hypertension, diabetes, dyslipidemias, cardiovascular disease, gall stones, osteoarthritis, and certain forms of cancers. Bringing about a weight loss can be used, for example, to reduce the likelihood of such diseases and as part of a treatment for such diseases. Weight reduction can be achieved by modulating MCH receptor activity to obtain, for example, one or more of the following effects: reducing appetite, increasing metabolic rate, reducing fat intake, or reducing carbohydrate craving.

Facilitating a weight gain, maintenance in weight, or appetite increase is particularly useful for a patient having a disease or disorder, or under going a treatment, accompanied by weight loss. Examples of diseases or disorders accompanied by weight loss include anorexia, bulimia, cancer cachexia, AIDS, wasting, cachexia, and wasting in frail elderly. Examples of treatments accompanied by weight loss include chemotherapy, radiation therapy, temporary or permanent immobilization, and dialysis.

MCH Receptor Nucleic Acid

The guidance provided in the present application can be used to obtain the MCH receptor from different sources such as mammalian sources and artificially produced MCH receptor. Identification and isolation of MCH receptor nucleic acid is preferably performed using MCH-R3 nucleic acid information. Such nucleic acid information can be used to facilitate obtaining a full length receptor.

Obtaining nucleic acids encoding for related polypeptides is facilitated using sets of degenerative probes and primers and by the proper selection of hybridization conditions. Sets of degenerative probes and primers are produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook et al., in *Molecular Cloning, A laboratory Manual*, 2$^{nd}$ Edition, Cold Spring Harbor Laboratory Press, 1989. PCR cloning techniques are described, for example, in White, *Methods in Molecular Cloning*, volume 67, Humana Press, 1997.

MCH receptor probes and primers can be used to screen nucleic acid libraries containing, for example, genomic DNA or cDNA. Such libraries are commercially available, and can be produced using techniques such as those described in Ausubel, *Current Protocols in Molecular Biology*, John Wiley, 1987–1998. Detection of probe hybridization is facilitated through the use of a detectable label.

Starting with a MCH receptor obtained from a particular source, derivatives can be produced having MCH receptor activity. Such derivatives include polypeptides having amino acid substitutions, additions and deletions. Such changes should be made outside of the MCH binding domain and in a manner not altering the tertiary structure. Amino acids are classified into certain types based on the structure of their R-groups. Substituting different amino acids within a particular group, such as substituting valine for leucine, arginine for lysine, and asparagine for glutamine may not cause a change in functionality of the polypeptide.

Starting with a particular MCH receptor amino acid sequence and the known degeneracy of the genetic code, a large number of different encoding nucleic acid sequences can be obtained. The degeneracy of the genetic code arises because almost all amino acids are encoded for by different combinations of nucleotide triplets. The translation of a particular codon into a particular amino acid is well known in the art (see, e.g., Lewin *GENES IV*, p. 119, Oxford University Press, 1990).

Nucleic acid having a desired sequence can be synthesized using chemical and biochemical techniques. Examples of such techniques are described in Ausubel, *Current Protocols in Molecular Biology*, John Wiley, 1987–1998, and Sambrook, et al., in *Molecular Cloning, A Laboratory Manual*, 2$^{nd}$ Edition, Cold Spring Harbor Laboratory Press, 1989.

Biochemical synthesis techniques involve the use of nucleic acid replicating conditions. Preferably, such techniques involve the use of a plasmid containing MCH receptor nucleic acid and a compatible host cell. Examples of suitable techniques are provided by Ausubel, *Current Protocols in Molecular Biology*, John Wiley, 1987–1998, and Sambrook, et al., in *Molecular Cloning, A Laboratory Manual*, 2$^{nd}$ Edition, Cold Spring Harbor Laboratory Press, 1989.

Nucleic acid obtained from a particular source can be altered using different techniques such as those provided for in Ausubel, *Current Protocols in Molecular Biology*, John Wiley, 1987–1998, and Sambrook, et al., in *Molecular Cloning, A laboratory Manual*, 2$^{nd}$ Edition, Cold Spring Harbor Laboratory Press, 1989.

Recombinant Expression

MCH receptor polypeptides such as a MCH receptor, a MCH receptor fragment, and a polypeptide containing the MCH receptor or MCH receptor fragment can be expressed from recombinant nucleic acid in vivo using a suitable host or in vitro using a translation system. Recombinantly expressed MCH receptor polypeptides are preferably used in assays to screen for compounds that bind to the MCH receptor and modulate the activity of the receptor.

Techniques for nucleic acid expression are well known in the art and can be applied to different nucleic acids encoding for different MCH receptor polypeptides. Examples of techniques for expression of nucleic acids are provided in Ausubel, *Current Protocols in Molecular Biology*, John Wiley, 1987–1998, and Sambrook, et al., in *Molecular*

*Cloning, A Laboratory Manual*, 2$^{nd}$ Edition, Cold Spring Harbor Laboratory Press, 1989.

Preferably, expression is achieved in a host cell using an expression vector. An expression vector contains nucleic acid encoding for a desired polypeptide along with regulatory elements for proper transcription and processing. Generally, the regulatory elements that are present include a transcriptional promoter, a ribosome binding site, a terminator, and an optionally present operator. Another preferred element is a polyadenylation signal providing for processing in eukaryotic cells. Examples of expression vectors are cloning vectors, modified cloning vectors, specifically designed plasmids and viruses.

Preferably, an expression vector also contains an origin of replication for autonomous replication in a host cell, a selectable marker, a limited number of useful restriction enzyme sites, and a potential for high copy number.

The skilled artisan can readily identify expression vectors providing suitable levels of MCH receptor polypeptide expression in different hosts. A variety of mammalian expression vectors are well known in the art including pcDNA3 (Invitrogen), pMC1neo (Stratagene), pXT1 (Stratagene), pSG5 (Stratagene), EBO-pSV2-neo (ATCC 37593) pBPV-1 (8–2), (ATCC 37110), pdBPV-MMTneo (342–12) (ATCC 37224), pRSVgpt (ATCC 37199), pRSVneo (ATCC 37198), pSV2-dhfr (ATCC 37565). A variety of bacterial expression vectors are well known in the art including pET11a (Novagen), lambda gt11 (Invitrogen), pcDNAII (Invitrogen), and pKK223-3 (Pharmacia). A variety of fungal cell expression vectors are well known in the art including pYES2 (Invitrogen), *Pichia* expression vector (Invitrogen). A variety of insect cell expression vectors are well known in the art including Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as *Drosophila* and silkworm derived cell lines. Commercially available mammalian cell lines include L cells L-M (TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

Expression vectors may be introduced into host cells using standard techniques. Examples of such techniques include transformation, transfection, lipofection, protoplast fusion, and electroporation.

MCH receptor nucleic acid can be expressed in a cell without the use of an expression vector using, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be performed, for example, by microinjection.

MCH-R3 Probes

Detection probes for MCH-R3 preferably contain a region targeted to a SEQ. ID. NO. 7 nucleic acid region. The targeted region has at least 16 nucleotides that hybridize (e.g., A-T and G-C hybridization) to a complementary region of 20 contiguous nucleotides present in SEQ. ID. NO. 7 or the complement thereof. Such probes can contain additional nucleic acid outside the targeted region to, for example, provide for increased specificity or the serve another purpose such as being a reporter sequence or a capture sequence.

Probes for the MCH receptor can specifically hybridize to MCH receptor target nucleic acid under appropriate hybridization conditions (i.e., distinguish target nucleic acid from one or more non-target nucleic acid molecules). Hybridization occurs through complementary nucleotide bases present on the probe or primer and MCH receptor nucleic acid. Hybridization conditions determine whether two molecules have sufficiently strong interactions with each other to form a stable hybrid.

Probes are composed of nucleic acids or derivatives thereof such as modified nucleic acid and peptide nucleic acid. Modified nucleic acid includes nucleic acid with one or more altered sugar groups, altered internucleotide linkages, and/or altered nucleotide purine or pyrimidine bases. Detection of probe hybridization is facilitated through the use of a detectable label. Examples of detectable labels include luminescent, enzymatic, and radioactive labels. References describing modified nucleic acid include WO 98/02582, U.S. Pat. No. 5,859,221 and U.S. Pat. No. 5,852,188, each of which are hereby incorporated by reference herein.

The degree of interaction between two molecules that hybridize together is reflected by the Tm of the produced hybrid. The higher the Tm the stronger the interactions and the more stable the hybrid. Tm is effected by numerous factors well known in the art such as the degree of complementarity, the type of complementary bases present (e.g., A-T hybridization versus G-C hybridization), and the structure of the nucleic acid backbones. E.g., Sambrook, et al., in *Molecular Cloning, A Laboratory Manual*, 2$^{nd}$ Edition, Cold Spring Harbor Laboratory Press, 1989.

Stable hybrids are formed when the Tm of a hybrid is greater than the temperature employed under a particular set of hybridization assay condition. The degree of specificity of a probe can be varied allowing for the identification of related sequences by adjusting the hybridization stringency conditions. Examples of stringency conditions are provided in Sambrook, et al., in *Molecular Cloning, A Laboratory Manual*, 2$^{nd}$ Edition, Cold Spring Harbor Laboratory Press, 1989.

An example of high stringency conditions is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hours at 65° C. in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.1% SDS. This is followed by a wash in 0.1×SSC, 0.1% SDS at 50° C. for 45 minutes before autoradiography. Other procedures using conditions of high stringency would include, for example, either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

MCH-R2/MCH-R3 Antibodies

Antibodies recognizing a MCH-R2 or MCH-R3 polypeptide can be produced using a SEQ. ID. NO. 8 polypeptide or a fragment thereof as an immunogen. Fragments of SEQ. ID. NO. 8 polypeptides used as an immunogen should be at least 9 amino acids in length. Antibodies to MCH-R3 can be used, for example, to identify and isolate MCH-R3 polypeptides. Examples of techniques for producing and using antibodies are described in Ausubel, *Current Protocols in Molecular Biology*, John Wiley, 1987–1998, Harlow, et al., *Antibodies, A Laboratory Manual*, Cold Spring Harbor Laboratory, 1988, and Kohler, et al., *Nature* 256:495–497 (1975).

MCH Receptor Binding Assay

MCH-R2, MCH-R3, and fragments thereof, can be used in a binding assay to screen compounds able to bind to the MCH receptor. Different types of assay formats can be employed including the use of labeled compounds and/or the use of a labeled MCH ligand.

The particular amino acid sequence involved in MCH receptor binding can be readily identified by using labeled MCH and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding MCH can be subdivided to further locate the MCH binding region. Fragments used for binding studies can be generated using recombinant nucleic acid techniques.

MCH ligands able to bind to the MCH receptor can readily be designed based on the structure of MCH and the ability of MCH derivatives to bind to the MCH receptor. Examples of different polypeptides that appear to be MCH ligands are provided for in U.S. Pat. No. 5,849,708, hereby incorporated by reference herein.

Different types of labels for MCH ligands can be employed. Examples of such labels include radiolabels, luminescent molecules, haptens and enzyme substrates. The ability of a particular label to interfere with binding can readily be determined by comparing the ability of MCH labeled with the particular label to compete against [$^{125}$I]-MCH binding.

Binding assays can be performed using individual compounds or preparations containing different numbers of compounds. A preparation containing different numbers of compounds having the ability to bind to the MCH receptor can be divided into smaller groups of compounds that can be tested to identify the compound(s) binding to the MCH receptor. In an embodiment of the present invention a test preparation containing at least 10 compounds is used in a binding assay.

Binding assays can be performed using recombinantly produced MCH receptor polypeptides present in different environments. Such environments include, for example, cell extracts, and purified cell extracts, containing the MCH receptor polypeptide expressed from recombinant nucleic acid; and also include, for example, the use of a purified MCH receptor polypeptide produced by recombinant means which is introduced into a different environment.

Screening For MCH Receptor Active Compounds

Screening for MCH receptor active compounds is facilitated using recombinantly expressed MCH-R2, MCH-R3 or a chimeric receptor containing a fragment thereof functionally coupled to a G protein. Using such recombinantly expressed MCH receptor polypeptides offers several advantages such as the ability to express the receptor in a defined cell system so that a response to MCH receptor active compounds can more readily be differentiated from responses to other receptors. For example, the MCH receptor can be expressed in a cell line such as HEK 293, COS 7, and CHO not normally expressing the receptor by an expression vector, wherein the same cell line without the expression vector or with an expression vector not encoding for a MCH receptor can act as a control.

Screening for MCH receptor active compounds is facilitated through the use of a MCH ligand in the assay. The use of a MCH ligand in a screening assay provides for MCH receptor activity. The effect of test compounds on such activity can be measured to identify, for example, allosteric modulators and antagonists. Additionally, such assays can be used to identify agonists.

MCH receptor activity can be measured using different techniques such as detecting a change in the intracellular conformation of the MCH receptor, G protein activities, and/or intracellular messengers. G protein activities include Gi and Gs. Gi activity can be measured using techniques well known in the art such as a melonaphore assay, assays measuring cAMP production, inhibition of cAMP accumulation, and binding of $^{35}$S-GTP. cAMP can be measured using different techniques such as radioimmunoassay and indirectly by cAMP responsive gene reporter proteins.

MCH receptor activity can be measured, for example, by assays measuring the phospholipase C signal transduction pathway. Activity of the phospholipase C signal transduction pathway can be measured using standard techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G protein activity is HEK293/aeq17. (Button et al., 1993. *Cell Calcium* 14, 663–671, and Feighner et al., 1999. *Science* 284:2184–2188, both of which are hereby incorporated by reference herein.)

Chimeric receptors containing one or more MCH receptor regions functionally coupled to polypeptides from other G proteins can also be used to measure activity. A chimeric MCH receptor contains an N-terminal extracellular domain; a transmembrane domain made up of transmembrane regions, extracellular loop regions, and intracellular loop regions; and an intracellular carboxy terminus domain.

The specificity of G protein coupling is determined by intracellular domain(s). A chimeric G protein coupled receptor can be produced to functionally couple to a particular G protein such as a Gq protein or a Gi protein. Such signal swapping allows for the detection of a receptor activity by measuring Gq or Gi activity. Techniques for producing chimeric receptors and measuring G protein coupled responses are provided for in, for example, International Application No. WO 97/05252, and U.S. Pat. No. 5,264,565, both of which are hereby incorporated by reference herein.

Functional assays can be performed using individual compounds or preparations containing different compounds. A preparation containing different compounds where one or more compounds affect MCH receptor or chimeric receptor activity can be divided into smaller groups of compounds to identify the compound(s) affecting MCH receptor activity. In an embodiment of the present invention a test preparation containing at least 10 compounds is used in a functional assay.

Functional assays can be performed using recombinantly produced MCH receptor polypeptides or chimeric receptor polypeptides present in different environments. Such environments include, for example, cell extracts, and purified cell extracts, containing the MCH receptor polypeptide expressed from recombinant nucleic acid; and the use of a purified MCH receptor polypeptide produced by recombinant means that is introduced into a different environment.

Preferably, recombinantly expressed MCH receptor polypeptide is expressed from an expression vector. More preferably, the recombinantly expressed MCH receptor polypeptide comprises or consists of an amino acid sequence provided for in SEQ. ID. NOs. 4 or 6.

Modulating MCH Receptor Expression

MCH receptor expression can be altered as a means for increasing or decreasing MCH receptor activity. Such alterations include inhibiting MCH receptor nucleic acid activity to reduce MCH receptor expression and supplying MCH receptor nucleic acid to increase MCH receptor activity.

Inhibition Of MCH Receptor Nucleic Acid Activity

MCH receptor nucleic acid activity can be inhibited using nucleic acids recognizing MCH receptor nucleic acid and affecting the ability of such nucleic acid to be transcribed or translated. Inhibition of MCH receptor nucleic acid activity can be used, for example, in target validation studies looking at appetite and stress in model systems, and to inhibit appetite or stress.

A preferred target for inhibiting MCH receptor translation is mRNA. The ability of mRNA to be translated into a protein can be effected by compounds such as anti-sense nucleic acid and enzymatic nucleic acid.

Anti-sense nucleic acid can hybridize to a region of a target mRNA. Depending on the structure of the anti-sense nucleic acid, anti-sense activity can be brought about by different mechanisms such as blocking the initiation of translation, preventing processing of mRNA, hybrid arrest, and degradation of mRNA by RNAse H activity.

Enzymatic nucleic acid can recognize and cleave another nucleic acid molecule. Preferred enzymatic nucleic acids are ribozymes.

General structures for anti-sense nucleic acids and ribozymes and methods of delivering such molecules are well known in the art. Modified and unmodified nucleic acids can be used to exert anti-sense effects. Different types of modifications can effect certain anti-sense activities such as the ability to be cleaved by RNAse H, and can effect nucleic acid stability. Examples of references describing different anti-sense molecules and ribozymes, and the use of such molecules are provided in U.S. Pat. Nos. 5,849,902, 5,859,221, and 5,852,188, which are each hereby incorporated by reference herein.

Guidelines for pharmaceutical administration in general are provided in, for example, Remington's Pharmaceutical Sciences 18$^{th}$ Edition, Ed. Gennaro, Mack Publishing, 1990, and Modern Pharmaceutics 2$^{nd}$ Edition, Eds. Banker and Rhodes, Marcel Dekker, Inc., 1990. Nucleic acid can be introduced into cells present in different environments using in vitro, in vivo, or ex vivo techniques.

Increasing MCH Receptor Expression

Nucleic acid coding for the MCH receptor can be used, for example, to cause an increase in appetite and to create a test system (e.g., a transgenic animal) for screening for compounds affecting MCH receptor expression. Nucleic acids can be introduced and expressed in cells present in different environments. Guidelines for pharmaceutical administration in general are provided in, for example, Remington's Pharmaceutical Sciences 18$^{th}$ Edition, supra. and Modern Pharmaceutics 2$^{nd}$ Edition, supra. Examples of techniques useful in gene therapy are illustrated in Gene Therapy & Molecular Biology: From Basic Mechanisms to Clinical Applications, Ed. Boulikas, Gene Therapy Press, 1998 (hereby incorporated by reference herein).

Modulating MCH Receptor Activity

Using the present application as a guide compounds able to modulate MCH receptor activity can be obtained and used to achieve a beneficial effect in a patient. Such effects can be achieved, for example, by altering appetite or relieving stress using a compound active at the MCH receptor.

Altering appetite is particularly useful for gaining weight in an under weight patient or losing weight in an over weight patient. In addition, for example, farm animals can be treated to gain weight. Under weight patients include those having a body weight about 10% or less, 20% or less, and 30% or less, than the lower end of a "normal" weight range or Body Mass Index ("BMI"). Over weight patients include those having a body weight about 10% or more, 20% or more, 30% or more, or 50% or more, than the upper end of a "normal" weight range or BMI. "Normal" weight ranges are well known in the art and take into account factors such as a patient age, height, and body type.

BMI measures your height/weight ratio. It is determined by calculating weight in kilograms divided by the square of height in meters. The BMI "normal" range is 19–22.

Preferably, non-protein MCH receptor antagonists are used to alter MCH receptor activity. Such antagonists are preferably organic compounds comprising one or more aryl or heteroaryl and having a molecule weight between about 150 and 900.

MCH receptor antagonists include compounds binding to the MCH receptor binding site and compounds binding at other sites. Such compounds can be identified using the techniques described herein. Preferably, an MCH receptor antagonist binds with an affinity of at least about 0.001-fold as well [$^{125}$I]-MCH using the in vitro MCH binding assay, or has an IC$_{50}$ of at least 5 µM as determined by the in vitro MCH binding assay or the melanophore assay (using e.g., MCH at a concentration of 150 nM in 0.1N acetic acid and MCH-R3). In additional embodiments, the antagonist binds at least 0.01-fold, or at least 0.1-fold, as well as [$^{125}$I]-MCH, or 0.1-fold to 0.05-fold as well as [$^{125}$I]-MCH using the in vitro MCH binding assay; and the MCH receptor antagonist has an IC$_{50}$ of at least 500 nM.

MCH receptor modulating compounds can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days.

Preferred kits contain a MCH receptor antagonist provided in dosage forms, wherein the antagonist binds with an affinity of at least about 0.001-fold as well as [$^{125}$I]-MCH using the in vitro MCH binding assay or has an IC$_{50}$ of at least about 5 µM. More preferably, the kits contain instructions indicating the use of the dosage form for weight reduction (e.g., obesity or overweight) or stress reduction, and the amount of dosage form to be taken over a specified time period.

Dosing For Therapeutic Applications

Guidelines for pharmaceutical administration in general are provided in, for example, Remington's Pharmaceutical Sciences 18$^{th}$ Edition, Ed. Gennaro, Mack Publishing, 1990, and Modern Pharmaceutics 2$^{nd}$ Edition, Eds. Banker and Rhodes, Marcel Dekker, Inc., 1990, both of which are hereby incorporated by reference herein.

Compounds activity active at the MCH receptor having appropriate functional groups can be prepared as acidic or base salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

MCH receptor active compounds can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

When administered by nasal aerosol or inhalation, compositions can be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds may also be administered in intravenous (both bolus and infusion), intraperitoneal, subcutaneous, topical with or without occlusion, or intramuscular form, all using forms well known to those of ordinary skill in the pharmaceutical arts. When administered by injection, the injectable solutions or suspensions may be formulated using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Suitable dosing regimens for the therapeutic applications of the present invention are selected taking into factors well known in the art including age, weight, sex and medical condition of the patient; the severity of the condition to be treated; the route of administration; the renal and hepatic function of the patient; and the particular compound employed. Guidelines for pharmaceutical administration including pharmaceutical compositions are provided in, for example, *Remington's Pharmaceutical Sciences* $18^{th}$ *Edition*, supra. and *Modern Pharmaceutics* $2^{nd}$ *Edition*, supra.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a patient is expected to be between 0.01 and 1,000 mg per adult patient per day.

EXAMPLES

Examples are provided below to further illustrate different features and advantages of the present invention. The examples also illustrate useful methodology for practicing the invention. These examples do not limit the claimed invention.

Example 1

MCH Receptor Related Sequences

Human MCH receptor related sequences are provided as follows:

```
Human MCH-R1 Nucleic Acid Sequence (SEQ. ID. NO. 1)

ATGGACCTGGAAGCCTCGCTGCTGCCCACTGGTCCCAACGCCAGCAACAC

CTCTGATGGCCCCGATAACCTCACTTCGGCAGGATCACCTCCTCGCACGG

GGAGCATCTCCTACATCAACATCATCATGCCTTCGGTGTTCGGCACCATCT

GCCTCCTGGGCATCATCGGGAACTCCACGGTCATCTTCGCGGTCGTGAAG

AAGTCCAAGCTGCACTGGTGCAACAACGTCCCCGACATCTTCATCATCAA

CCTCTCGGTAGTAGATCTCCTCTTTCTCCTGGGCATGCCCTTCATGATCCA

CCAGCTCATGGGCAATGGGGTGTGGCACTTTGGGGAGACCATGTGCACCC

TCATCACGGCCATGGATGCCAATAGTCAGTTCACCAGCACCTACATCCTG

ACCGCCATGGCCATTGACCGCTACCTGGCCACTGTCCACCCCATCTCTTCC
```

-continued
ACGAAGTTCCGGAAGCCCTCTGTGGCCACCCTGGTGATCTGCCTCCTGTGG

GCCCTCTCCTTCATCAGCATCACCCCTGTGTGGCTGTATGCCAGACTCATC

CCCTTCCCAGGAGGTGCAGTGGGCTGCGGCATACGCCTGCCCAACCCAGA

CACTGACCTCTACTGGTTCACCCTGTACCAGTTTTTCCTGGCCTTTGCCCTG

CCTTTTGTGGTCATCACAGCCGCATACGTGAGGATCCTGCAGCGCATGAC

GTCCTCAGTGGCCCCCGCCTCCCAGCGCAGCATCCGGCTGCGGACAAAGA

GGGTGACCCGCACAGCCATCGCCATCTGTCTGGTCTTCTTTGTGTGCTGGG

CACCCTACTATGTGCTACAGCTGACCCAGTTGTCCATCAGCCGCCCGACCC

TCACCTTTGTCTACTTATACAATGCGGCCATCAGCTTGGGCTATGCCAACA

GCTGCCTCAACCCCTTTGTGTACATCGTGCTCTGTGAGACGTTCCGCAAAC

GCTTGGTCCTGTCGGTGAAGCCTGCAGCCCAGGGGCAGCTTCGCGCTGTC

AGCAACGCTCAGACGGCTGACGAGGAGAGGACAGAAAGCAAAGGCACCT

GA

Human MCH-R1 Amino Acid Sequence (SEQ. ID. NO. 2)

MDLEASLLPTGPNASNTSDGPDNLTSAGSPPRTGSISYINIIMPSVFGTICLLGIIG

NSTVIFAVVKKSKLHWCNNVPDIFIINLSVVDLLFLLGMPFMIHQLMGNGVWH

FGETMCTLITAMDANSQFTSTYILTAMAIDRYLATVHPISSTKFRKPSVATLVI

CLLWALSFISITPVWLYARLIPFPGGAVGCGIRLPNPDTDLYWFTLYQFFLAFA

LPFVVITAAYVRILQRMTSSVAPASQRSIRLRTKRVTRTAIAICLVFFVCWAPY

YVLQLTQLSISRPTLTFVYLYNAAISLGYANSCLNPFVYIVLCETFRKRLVLSV

KPAAQGQLRAVSNAQTADEERTESKGT

Human MCH-R2 Nucleic Acid Sequence (SEQ. ID. NO. 3)

ATGAAGAAGGGAGTGGGGAGGGCAGTTGGGCTTGGAGGCGGCAGCGGCT

GCCAGGCTACGGAGGAAGACCCCCTTCCCAACTGCGGGGCTTGCGCTCCG

GGACAAGGTGGCAGGCGCTGGAGGCTGCCGCAGCCTGCGTGGGTGGAGG

GGAGCTCAGCTCGGTTGTGGGAGCAGGCGACCGGCACTGGCTGGATGGAC

CTGGAAGCCTCGCTGCTGCCCACTGGTCCCAACGCCAGCAACACCTCTGA

TGGCCCCGATAACCTCACTTCGGCAGGATCACCTCCTCGCACGGGGAGCA

TCTCCTACATCAACATCATCATGCCTTCGGTGTTCGGCACCATCTGCCTCC

TGGGCATCATCGGGAACTCCACGGTCATCTTCGCGGTCGTGAAGAAGTCC

AAGCTGCACTGGTGCAACAACGTCCCCGACATCTTCATCATCAACCTCTCG

GTAGTAGATCTCCTCTTTCTCCTGGGCATGCCCTTCATGATCCACCAGCTC

ATGGGCAATGGGGTGTGGCACTTTGGGGAGACCATGTGCACCCTCATCAC

GGCCATGGATGCCAATAGTCAGTTCACCAGCACCTACATCCTGACCGCCA

TGGCCATTGACCGCTACCTGGCCACTGTCCACCCCATCTCTTCCACGAAGT

TCCGGAAGCCCTCTGTGGCCACCCTGGTGATCTGCCTCCTGTGGGCCCTCT

CCTTCATCAGCATCACCCCTGTGTGGCTGTATGCCAGACTCATCCCCTTCC

CAGGAGGTGCAGTGGGCTGCGGCATACGCCTGCCCAACCCAGACACTGAC

CTCTACTGGTTCACCCTGTACCAGTTTTTCCTGGCCTTTGCCCTGCCTTTTG

TGGTCATCACAGCCGCATACGTGAGGATCCTGCAGCGCATGACGTCCTCA

-continued

```
GTGGCCCCGCCTCCCAGCGCAGCATCCGGCTGCGGACAAAGAGGGTGAC

CCGCACAGCCATCGCCATCTGTCTGGTCTTCTTTGTGTGCTGGGCACCCTA

CTATGTGCTACAGCTGACCCAGTTGTCCATCAGCCGCCCGACCCTCACCTT

TGTCTACTTATACAATGCGGCCATCAGCTTGGGCTATGCCAACAGCTGCCT

CAACCCCTTTGTGTACATCGTGCTCTGTGAGACGTTCCGCAAACGCTTGGT

CCTGTCGGTGAAGCCTGCAGCCCAGGGGCAGCTTCGCGCTGTCAGCAACG

CTCAGACGGCTGACGAGGAGAGGACAGAAAGCAAAGGCACCTGA
```

Human MCH-R2 Amino Acid Sequence (SEQ. ID. NO. 4)

```
MKKGVGRAVGLGGGSGCQATEEDPLPNCGACAPGQGGRRWRLPQPAWVEG

SSARLWEQATGTGWMDLEASLLPTGPNASNTSDGPDNLTSAGSPPRTGSISYI

NIIMPSVFGTICLLGIIGNSTVIFAVVKKSKLHWCNNVPDLFIINLSVVDLLFLLG

MPFMIHQLMGNGVWHFGETMCTLITAMDANSQFTSTYILTAMAIDRYLATVH

PISSTKFRKPSVATLVICLLWALSFISITPVWLYARLIPFPGGAVGCGIRLPNPDT

DLYWFTLYQFFLAFALPFVVITAAYVRILQRMTSSVAPASQRSLRLRTKRVTRT

AIAICLVFFVCWAPYYVLQLTQLSISRPTLTFVYLYNAAISLGYANSCLNPFVYI

VLCETFRKRLVLSVKPAAQGQLRAVSNAQTADEERTESKGT
```

Human MCH-R3 Nucleic Acid Sequence (SEQ. ID. NO. 5)

```
ATGTCAGTGGGAGCCATGAAGAAGGGAGTGGGGAGGGCAGTTGGGCTTG

GAGGCGGCAGCGGCTGCCAGGCTACGGAGGAAGACCCCCTTCCCAACTGC

GGGGCTTGCGCTCCGGGACAAGGTGGCAGGCGCTGGAGGCTGCCGCAGC

CTGCGTGGGTGGAGGGGAGCTCAGCTCGGTTGTGGGAGCAGGCGACCGG

CACTGGCTGGATGGACCTGGAAGCCTCGCTGCTGCCCACTGGTCCCAACG

CCAGCAACACCTCTGATGGCCCCGATAACCTCACTTCGGCAGGATCACCT

CCTCGCACGGGGAGCATCTCCTACATCAACATCATCATGCCTTCGGTGTTC

GGCACCATCTGCCTCCTGGGCATCATCGGGAACTCCACGGTCATCTCGCG

GTCGTGAAGAAGTCCAAGCTGCACTGGTGCAACAACGTCCCCGACATCTT

CATCATCAACCTCTCGGTAGTAGATCTCCTCTTTCTCCTGGGCATGCCCTT

CATGATCCACCAGCTCATGGGCAATGGGGTGTGGCACTTTGGGGAGACCA

TGTGCACCCTCATCACGGCCATGGATGCCAATAGTCAGTTCACCAGCACC

TACATCCTGACCGCCATGGCCATTGACCGCTACCTGGCCACTGTCCACCCC

ATCTCTTCCACGAAGTTCCGGAAGCCCTCTGTGGCCACCCTGGTGATCTGC

CTCCTGTGGGCCCTCTCCTTCATCAGCATCACCCCTGTGTGGCTGTATGCC

AGACTCATCCCCTTCCCAGGAGGTGCAGTGGGCTGCGGCATACGCCTGCC

CAACCCAGACACTGACCTCTACTGGTTCACCCTGTACCAGTTTTTCCTGGC

CTTTGCCCTGCCTTTTGTGGTCATCACAGCCGCATACGTGAGGATCCTGCA

GCGCATGACGTCCTCAGTGGCCCCCGCCTCCCAGCGCAGCATCCGGCTGC

GGACAAAGAGGGTGACCCGCACAGCCATCGCCATCTGTCTGGTCTTCTTT

GTGTGCTGGGCACCCTACTATGTGCTACAGCTGACCCAGTTGTCCATCAGC

CGCCCGACCCTCACCTTTGTCTACTTATACAATGCGGCCATCAGCTTGGGC

TATGCCAACAGCTGCCTCAACCCCTTTGTGTACATCGTGCTCTGTGAGACG
```

-continued

```
TTCCGCAAACGCTTGGTCCTGTCGGTGAAGCCTGCAGCCCAGGGGCAGCT

TCGCGCTGTCAGCAACGCTCAGACGGCTGACGAGGAGAGGACAGAAAGC

AAAGGCACCTGA
```

Human MCH-R3 Amino Acid Sequence (SEQ. ID. NO. 6)

```
MSVGAMKKGVGRAVGLGGGSGCQATEEDPLPNCGACAPGQGGRRWRLPQP

AWVEGSSARLWEQATGTGWMDLEASLLPTGPNASNTSDGPDNLTSAGSPPR

TGSISYINIIMPSVFGTICLLGIIGNSTVIFAVVKKSKLHWCNNVPDIFIINLSVVD

LLFLLGMPFMIHQLMGNGVWHFGETMCTLITAMDANSQFTSTYILTAMAIDR

YLATVHPISSTKFRKPSVATLVICLLWALSFISITPVWLYARLIPFPGGAVGCGI

RLPNPDTDLYWFTLYQFFLAFALPFVVITAAYVRILQRMTSSVAPASQRSIRLR

TKRVTRTAIAICLVFFVCWAPYYVLQLTQLSISRPTLTFVYLYNAAISLGYANS

CLNPFVYIVLCETFRKRLVLSVKPAAQGQLRAVSNAQTADEERTESKGT
```

SEQ. ID. NO. 7

```
ATGTCAGTGGGAGCCATGAAGAAGGGAGTGGGGAGGGCAGTTGGGCTTG

GAGGCGGCAGCGGCTGCCAGGCTACGGAGGAAGACCCCCTTCCCAACTGC

GGGGCTTGCGCTCCGGGACAAGGTGGCAGGCGCTGGAGGCTGCCGCAGC

CTGCGTGGGTGGAGGGGAGCTCAGCTCGGTTGTGGGAGCAGGCGACCGG

CACTGGCTGG
```

SEQ. ID. NO. 8

```
MSVGAMKKGVGRAVGLGGGSGCQATEEDPLPNCGACAPGQGGRRWRLPQP

AWVEGSSARLWEQATGTGW
```

MCH-R3 DNA with Intron (lower case) SEQ. ID. NO. 9

```
ATGTCAGTGGGAGCCATGAAGAAGGGAGTGGGGAGGGCAGTTGGGCTTG

GAGGCGGCAGCGGCTGCCAGGCTACGGAGGAAGACCCCCTTCCCAACTGC

GGGGCTTGCGCTCCGGGACAAGGTGGCAGGCGCTGGAGGCTGCCGCAGC

CTGCGTGGGTGGAGGGGAGCTCAGCTCGGTTGTGGGAGCAGGCGACCGG

CACTGGCTGGATGGACCTGGAAGCCTCGCTGCTGCCCACTGGTCCCAACG

CCAGCAACACCTCTGATGGCCCCGATAACCTCACTTCGGCAGgtgagttgactggg agccctcctcctctgggctgtgggtggaaaatgggaaggtttcaccccctgagccaaactgcttgggaaactttatcacagtt cttggggacaagatctgtggtctgctttgctctgaggggcaggagaaaaggggggcaatggtccgcaggggcagacgggc aggagcagagcaggggggcgaaggcatattcagaatggcaaggaaggggggccagccgtgagacagcaggggaaggc tcgctgctgggttccaaagatgcttggcagaaaaaattccaggctggaaaagcaagcgagagaagctggagggtggtatgt gggagacagctgggggctcactcctgcactgttagcctcagcttttttactcccacttggatgatgaggtctgagacatccttac tgccacctgggagaggccctgggaagggaagacttcacagagccatgagggggattaacttttctggtgaattaagcttcctg acatttccagagctgcggtgccctgggattccagctttgaaggagaaaggaaggaaggaaaagaggaaaggcttatgtag ataattttccaggctgctgagctccaacagacagtttctgtctctgcttcactcaagaagcccaggctcagaagataccaatc aaggaaatccccgctaggaagcctggggtaggagagctgctggcttgaccagggcacagccggcaaaagcctctacaa gacagtcacccacagatatgcccaagaatcagtacacagutccaaccagagatctccaaaatgaaacactcagggctaca cataggaaaagcacgcacacacacacacacacatacacagagacacttacttttgtgtccttctggctatgctgacgagttttc ctggtgaagcccggggctcacagagtaatctctgcagacaactgtggttcttgcctctggtgcctgcaggaggcaggcatgt
```

-continued

```
tgtgtccttccaagacagatggctcagggcactctggtaggattcaccaggaaactcatggagaagggaaagggacaag attagcaacagtgaagggagggagaatggtgggagaggattccagatgaacggtgggtcgctggaggctgagcatgcca gcaggatgtcagttctcagagcaaagcccatgtcaaacagccaacgcttgctccttctgtccccagGATCACCTCC

TCGCACGGGGAGCATCTCCTACATCAACATCATCATGCCTTCGGTGTTCGG

CACCATCTGCCTCCTGGGCATCATCGGGAACTCCACGGTCATCTTCGCGGT

CGTGAAGAAGTCCAAGCTGCACTGGTGCAACAACGTCCCCGACATCTTCA

TCATCAACCTCTCGGTAGTAGATCTCCTCTTTCTCCTGGGCATGCCCTTCAT

GATCCACCAGCTCATGGGCAATGGGGTGTGGCACTTTGGGGAGACCATGT

GCACCCTCATCACGGCCATGGATGCCAATAGTCAGTTCACCAGCACCTAC

ATCCTGACCGCCATGGCCATTGACCGCTACCTGGCCACTGTCCACCCCATC

TCTTCCACGAAGTTCCGGAAGCCCTCTGTGGCCACCCTGGTGATCTGCCTC

CTGTGGGCCCTCTCCTTCATCAGCATCACCCCTGTGTGGCTGTATGCCAGA

CTCATCCCCTTCCCAGGAGGTGCAGTGGGCTGCGGCATACGCCTGCCCAA

CCCAGACACTGACCTCTACTGGTTCACCCTGTACCAGTTTTTCCTGGCCTT

TGCCCTGCCTTTTGTGGTCATCACAGCCGCATACGTGAGGATCCTGCAGCG

CATGACGTCCTCAGTGGCCCCCGCCTCCCAGCGCAGCATCCGGCTGCGGA

CAAAGAGGGTGACCCGCACAGCCATCGCCATCTGTCTGGTCTTCTLTGTGT

GCTGGGCACCCTACTATGTGCTACAGCTGACCCAGTTGTCCATCAGCCGCC

CGACCCTCACCTTTGTCTACTTATACAATGCGGCCATCAGCTTGGGCTATG

CCAACAGCTGCCTCAACCCCTTTGTGTACATCGTGCTCTGTGAGACGTTCC

GCAAACGCTTGGTCCTGTCGGTGAAGCCTGCAGCCCAGGGGCAGCTTCGC

GCTGTCAGCAACGCTCAGACGGCTGACGAGGAGAGGACAGAAAGCAAAG

GCACCTGA
```

Example 2

Melanophore Assay for Determination of G Protein-Coupled Receptor Activation Melanophores were transfected with either a vector designed to synthesize SLC-1 mRNA and thereby lead to overexpression of SLC-1 receptor (i.e., pcDNA3-hSLC-1), the empty vector (pcDNA3), and plasmids encoding control receptors (i.e., pcDNA1amp-CB2 and pcDNA3-thromboxane A2). The plasmid vector pcDNA3 (Invitrogen) was used to express the recombinant SLC-1 mRNA and protein in cells transfected with this construct. The coding sequence of the SLC-1 cDNA without its untranslated 5' and 3' sequences (SEQ. ID. NO. 1) was subcloned by blunt-end ligation into the EcoRV site of pcDNA3. The SLC-1 cDNA insert can be excised from pcDNA3-hSLC-1 by restriction digestion of the plasmid with KpnI and XbaI. The amino-terminal coding end of the SLC-1 insert was cloned proximal to the Cytomegalovirus promoter contained in pcDNA3. The carboxyl-terminal coding sequences of the SLC-1 insert was cloned proximal to the bovine growth hormone polyadenylation signal sequence in pcDNA3.

Growth of *Xenopus laevis* melanophores and fibroblasts was performed as described previously (Daniolos, et al., 1992. *Pigment Cell Res.* 3, 38–43; and Lerner, 1994. *Trends Neurol. Sci.* 17, 142–146). Briefly, melanophores were grown in *Xenopus* fibroblast-conditioned growth medium. The fibroblast-conditioned growth medium was prepared by growing *Xenopus* fibroblasts in 70% L-15 medium (Sigma), pH 7.3, supplemented with 20% heat inactivated fetal bovine serum (Life Technologies, Mississauga, Ont), 100 µg/ml streptomycin, 100 units/ml penicillin and 2 mM glutamine at 27° C. The medium from growing fibroblasts was collected, passed through a 0.2 micron filter (referred to as fibroblast-conditioned growth medium) and used to culture melanophores at 27° C. Plasmid DNA was transiently transfected into melanophores by electroporation using a BTX ECM600 electroporator (Genetronics, Inc. San Diego, Calif.).

Melanophores were incubated in the presence of fresh fibroblast-conditioned growth medium for 1 hour prior to harvesting of cells. Melanophore monolayers were detached by trypsinization (0.25% trypsin, JHR Biosciences, Lenexa, Kans.), followed by inactivation of the trypsin with fibroblast-conditioned growth medium.

The cells were collected by centrifugation at 200×g for 5 minutes at 4° C. Cells were washed once in fibroblast conditioned growth medium, centrifuged (200×g, 5 minutes, 4° C.) and resuspended at 5×10$^6$ cells per ml in ice cold 70% PBS pH 7.0 400 µl aliquots of cells in PBS were added to prechilled 1.5 ml tubes containing 2 µg of pcDNA3-hSLC-1 plasmid DNA, 2 µg each of two internal control GPCRs (pcDNA lamp-cannabinoid 2 and pcDNA3-thromboxane A2; Slipitz, et al., 1995. *Mol. Pharmacol.* 48, 352–361), and 18 μg of pcDNA3.1 plasmid vector DNA for a total of 24 μg DNA in a 40 μl total volume. Samples were incubated on ice for 20 minutes with mixing every 7 minutes.

Cell and DNA mixes were transferred to prechilled 0.2 mm gap electroporation cuvettes (BTX) and electroporated using the following settings: capacitance of 325 microfarad, voltage of 450 volts and resistance of 720 ohms. Immediately following electroporation, cells were mixed with fibroblast-conditioned growth medium and plated onto flat bottom 96 well microtiter plates (NUNC). Electroporations from multiple cuvettes were pooled together prior to plating to ensure homogenous transfection efficiency.

On the day following transfection, the media was replaced with fresh fibroblast-conditioned growth media and incubated for one to three days at 27° C. prior to assaying for receptor expression. On the day of ligand stimulation, medium was removed by aspiration and cells were washed with 70% L-15 media containing 15 mM HEPES, pH 7.3.

Assays were divided into two separate parts in order to examine Gs/Gq-coupling which results in pigment dispersion in melanophores, or Gi-coupling which results in pigment aggregation. For Gs/Gq-coupling responses, assays were performed as follows. Cells were incubated in 100 μl of 70% L-15 media containing 15 mM HEPES, pH 7.3, for 1 hour in the dark at room temperature, and then incubated in the presence of melatonin (2 nM final concentration) for 1 hour in the dark at room temperature to induce pigment aggregation. Initial absorbance readings at 600 nm were measured using a Bio-Tek Elx800 Microplate reader (ESBE Scientific) prior to addition of ligand. Ligands (100 nM final concentration in DMSO for small molecules non-peptides or 150 nM final concentration in 0.1N acetic acid for peptide molecules) were added to wells, mixed, and incubated in the dark at room temperature for 1 hour, after which the final absorbance at 600 nm was determined.

For Gi-coupled responses, cell monolayers plated in 96-well microtiter plates were incubated in the presence of 100 μl/well of 70% L-15 media containing 2% fibroblast-conditioned growth medium, 2 mM glutamine, 100 μg/ml streptomycin, 100 units/ml penicillin and 15 mM HEPES, pH 7.3, for 15 minutes in readings at 600 nm were determined, followed by the addition of ligands. After a 1.5 hour incubation in the dark at room temperature final absorbances were determined. Absorbance readings were converted to transmission values to quantitate pigment dispersion using the following formula: 1−Tf/Ti, where Ti=the initial transmission at 600 nm and Tf=the final transmission at 600 nm.

Example 3

MCH-R1 Receptor Activity

The *Xenopus* melanophore system (Daniolos, et al., 1992. *Pigment Cell Res.* 3, 38–43) is based on the dispersion and aggregation of intracellular pigment granules in response to changes in intracellular second messenger molecules. Agonist activation of a recombinant Gs- or Gq-coupled receptor expressed heterologously in melanophores leads to pigment dispersion. Conversely, agonist activation of a recombinant Gi-coupled receptor expressed heterologously in melanophores leads to pigment aggregation. Changes in the melanophore pigmentation show a dose-dependent correlation with the level of specific receptor activation, and can be quantified by the change in absorbance at 600 nm between the nonactivated and agonist-activated cells (Daniolos, et al., 1992. Pigment Cell Res. 3, 38–43).

Melanophores transiently transfected with plasmid DNAs expressing "SLC-1", cannabinoid 2 and thromboxane A2 receptors were plated onto 96 well microtiter plates. Following the above pretreatment conditions, cells were incubated for 1 hour in the presence of a collection of 202 known small molecules and peptides including MCH. The test ligand collection included 80 small molecules (a different test molecule in each well) at 100 nM final concentration, 80 peptides at 150 nM final concentration and 42 small molecules and peptides at 500 and 1000 nM final concentration, respectively.

Pigment aggregation responses (Gi-coupled responses) were detected with the following five peptides from the peptide plate (150 nM final concentration): thrombin, MCH, valosin, RANTES and CGRP with responses ranging from 33% to 66% of the positive cannabinoid 2 receptor control activated by the cannabinoid receptor agonist, HU-210. Background aggregation responses in this assay range from 0–25% of the positive control cannabinoid 2 receptor response. The response seen for thrombin is detected in mock (non-receptor) transfected melanophores and represents activation of the endogenous melanophore thrombin receptor. Other controls include a positive aggregation response to melatonin, stimulating the endogenous *Xenopus* receptor and a lack of aggregation response to PBS, acetic acid or DMSO vehicle controls (15%, 11% and 3% of the positive cannabinoid 2 receptor positive control value, respectively).

Example 4

MCH Receptor Binding Assay

The MCH receptor binding assay can be conducted on cells transfected with a MCH-R2 expression plasmid (full-length open reading frame of SEQ. ID. NO. 5 placed in the mammalian expression vector pcDNA-3 (Invitrogen, Carlsbad, Calif.) or a MCH-R2 expression plasmid (full-length open reading frame of SEQ. ID. NO. 3 placed in the mammalian expression vector pcDNA-3 (Invitrogen, Carlsbad, Calif.) to produce a MCH-R expression plasmid. Mammalian cells HEK-293 or COS-7 are transfected with vector using Lipofectamine (GIBCO-BRL; Hawley-Nelson, P. 1993, Focus 15:73). Transfections are performed in 60 mm dishes on 80% confluent cells (approximately $4 \times 10^5$ cells) with 8 μg of Lipofectamine and 32 μg of MCH-R plasmid DNA.

Binding of [$^{125}$I]-MCH is measured using crude membranes prepared from HEK-293 or COS-7 cells transfected with MCH-R expression plasmids. Crude cell membranes from COS-7 or HEK-293 transfectants are prepared on ice, 48 hours post-transfection. Each 60 mm dish is washed twice with 3 ml of PBS, once with 1 ml homogenization buffer (50 mM Tris-HCl [pH 7.4], 5 mM $MgCl_2$, 2.5 mM EDTA, 30 μg/ml bacitracin, 1 μM phosphoramidon, 0.2% BSA). 0.5 ml of homogenization buffer is added to each dish, cells are removed by scraping and then homogenized using a Polytron device (Brinkmann, Syosset, N.Y.; 3 bursts of 10 sec. at setting 4). The homogenate is then centrifuged for 20 minutes at 11,000×g at 0° C. and the resulting crude membrane pellet (chiefly containing cell membranes and nuclei) is resuspended in homogenization buffer supplemented with 0.06% BSA (0.1 ml/60 mm dish) and kept on ice.

Binding reactions are performed at 20° C. for 1 hour in a total volume of 0.5 ml containing: 0.1 ml of membrane suspension, 10 μg of [$^{125}$I]-MCH (0.05 to 1 nM; specific activity approximately 2000 Ci/mmol), 10 μl of competing compound(s) and 380–390 μl of homogenization buffer. Bound radioligand is separated by rapid vacuum filtration (Brandel 48-well cell harvester) through GF/C filters pretreated for the filter, the filters are washed 3 times with 3 ml each of ice cold 50 mM Tris-HCl [pH 7.4], 10 mM MgCl2, 2.5 mM EDTA and 0.015% Triton X-100, and the bound radioactivity on the filers is quantitated by gamma counting.

Specific binding (>90% of total) is defined as the difference between total binding and non-specific binding conducted in the presence of 100 nM unlabeled MCH.

Other embodiments are within the following claims. While several embodiments have been shown and described, various modifications may be made without departing from the spirit and scope of the present invention.

What is claimed is:

1. A purified nucleic acid comprising a nucleotide sequence encoding for SEQ ID NO: 4 or SEQ ID NO: 6.

2. The nucleic acid of claim 1, wherein said nucleic acid comprises the nucleotide sequence of SEQ. ID. NO. 3.

3. The nucleic acid of claim 1, wherein said nucleotide sequence encodes for the amino acid sequence of SEQ. ID. NO. 4.

4. The nucleic acid of claim 1, wherein said nucleic acid comprises the nucleotide sequence of SEQ. ID. NO. 5.

5. The nucleic acid of claim 1, wherein said nucleotide sequence encodes for the amino acid sequence of SEQ. ID. NO. 6.

6. An expression vector comprising a nucleotide sequence encoding for SEQ ID NO: 4 or SEQ ID NO: 6.

7. The expression vector of claim 6, wherein said nucleotide sequence is functionally coupled to an exogenous promoter.

8. The expression vector of claim 7, wherein said expression vector comprises the nucleotide sequence of SEQ. ID. NO. 3.

9. The expression vector of claim 7, wherein said nucleotide sequence encodes the amino acid sequence of SEQ. ID. NO. 4.

10. The expression vector of claim 7, wherein said expression vector comprises the nucleotide sequence of SEQ. ID. NO. 5.

11. The expression vector of claim 7, wherein said nucleotide sequence encodes the amino acid sequence of SEQ. ID. NO. 6.

12. A isolated cell comprising the expression vector of claim 6.

13. A method of preparing a MCH receptor polypeptide comprising the step of growing the cell of claim 12 under conditions wherein said polypeptide is expressed from said expression vector and isolate the polypeptide.

* * * * *

SEQUENCE LISTING

<160> NUMBER OF SEQ ID NOS: 10

<210> SEQ ID NO 1
<211> LENGTH: 1062
<212> TYPE: DNA
<213> ORGANISM: Human

<400> SEQUENCE: 1

```
atggacctgg aagcctcgct gctgcccact ggtcccaacg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg gcatcatcgg gaactccacg     180
gtcatcttcg cggtcgtgaa gaagtccaag ctgcactggt gcaacaacgt ccccgacatc     240
ttcatcatca acctctcggt agtagatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccactgtcca ccccatctct tccacgaagt tccggaagcc ctctgtggcc     480
accctggtga tctgcctcct gtgggccctc tccttcatca gcatcacccc tgtgtggctg     540
tatgccagac tcatcccctt cccaggaggt gcagtgggct gcggcatacg cctgcccaac     600
ccagacactg acctctactg gttcaccctg taccagtttt tcctggcctt tgccctgcct     660
tttgtggtca tcacagccgc atacgtgagg atcctgcagc gcatgacgtc ctcagtggcc     720
cccgcctccc agcgcagcat ccggctgcgg acaaagaggg tgacccgcac agccatcgcc     780
atctgtctgg tcttctttgt gtgctgggca ccctactatg tgctacagct gacccagttg     840
tccatcagcc gcccgacccc caccttttgtc tacttataca atgcggccat cagcttgggc     900
tatgccaaca gctgcctcaa cccctttgtg tacatcgtgc tctgtgagac gttccgcaaa     960
cgcttggtcc tgtcggtgaa gcctgcagcc caggggcagc ttcgcgctgt cagcaacgct    1020
cagacggctg acgaggagag gacagaaagc aaaggcacct ga                       1062
```

<210> SEQ ID NO 2
<211> LENGTH: 353
<212> TYPE: PRT
<213> ORGANISM: Human

<400> SEQUENCE: 2

```
Met Asp Leu Glu Ala Ser Leu Leu Pro Thr Gly Pro Asn Ala Ser Asn
 1               5                   10                  15

Thr Ser Asp Gly Pro Asp Asn Leu Thr Ser Ala Gly Ser Pro Pro Arg
             20                  25                  30

Thr Gly Ser Ile Ser Tyr Ile Asn Ile Ile Met Pro Ser Val Phe Gly
         35                  40                  45

Thr Ile Cys Leu Leu Gly Ile Ile Gly Asn Ser Thr Val Ile Phe Ala
     50                  55                  60
```

-continued

```
Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr
```

<210> SEQ ID NO 3
<211> LENGTH: 1254
<212> TYPE: DNA
<213> ORGANISM: Human

<400> SEQUENCE: 3

| | | |
|---|---|---|
| atgaagaagg gagtggggag ggcagttggg cttggaggcg gcagcggctg ccaggctacg | 60 |
| gaggaagacc cccttcccaa ctgcggggct tgcgctccgg acaaggtgg caggcgctgg | 120 |
| aggctgccgc agcctgcgtg gtggaggg agctcagctc ggttgtggga gcaggcgacc | 180 |
| ggcactggct ggatggacct ggaagcctcg ctgctgccca ctggtcccaa cgccagcaac | 240 |
| acctctgatg ccccgataa cctcacttcg gcaggatcac ctcctcgcac ggggagcatc | 300 |
| tcctacatca acatcatcat gccttcggtg ttcggcacca tctgcctcct gggcatcatc | 360 |
| gggaactcca cggtcatctt cgcggtcgtg aagaagtcca agctgcactg gtgcaacaac | 420 |
| gtccccgaca tcttcatcat caacctctcg gtagtagatc tcctctttct cctgggcatg | 480 |

```
ccccttcatga tccaccagct catgggcaat ggggtgtggc actttgggga gaccatgtgc      540
accctcatca cggccatgga tgccaatagt cagttcacca gcacctacat cctgaccgcc      600
atggccattg accgctacct ggccactgtc caccccatct cttccacgaa gttccggaag      660
ccctctgtgg ccaccctggt gatctgcctc ctgtgggccc tctccttcat cagcatcacc      720
cctgtgtggc tgtatgccag actcatcccc ttcccaggag gtgcagtggg ctgcggcata      780
cgcctgccca acccagacac tgacctctac tggttcaccc tgtaccagtt tttcctggcc      840
tttgccctgc cttttgtggt catcacagcc gcatacgtga ggatcctgca gcgcatgacg      900
tcctcagtgg cccccgcctc ccagcgcagc atccggctgc ggacaaagag ggtgacccgc      960
acagccatcg ccatctgtct ggtcttcttt gtgtgctggg cacccctacta tgtgctacag     1020 ctgacccagt tgtccatcag ccgcccgacc ctcacctttg tctacttata caatgcggcc     1080
atcagcttgg gctatgccaa cagctgcctc aaccccttcg tgtacatcgt gctctgtgag     1140
acgttccgca aacgcttggt cctgtcggtg aagcctgcag cccagggggca gcttcgcgct     1200 gtcagcaacg ctcagacggc tgacgaggag aggacagaaa gcaaaggcac ctga           1254
```

<210> SEQ ID NO 4
<211> LENGTH: 417
<212> TYPE: PRT
<213> ORGANISM: Human

<400> SEQUENCE: 4

```
Met Lys Lys Gly Val Gly Arg Ala Val Gly Leu Gly Gly Gly Ser Gly
 1               5                  10                  15

Cys Gln Ala Thr Glu Glu Asp Pro Leu Pro Asn Cys Gly Ala Cys Ala
            20                  25                  30

Pro Gly Gln Gly Gly Arg Arg Trp Arg Leu Pro Gln Pro Ala Trp Val
        35                  40                  45

Glu Gly Ser Ser Ala Arg Leu Trp Glu Gln Ala Thr Gly Thr Gly Trp
    50                  55                  60

Met Asp Leu Glu Ala Ser Leu Leu Pro Thr Gly Pro Asn Ala Ser Asn
65                  70                  75                  80

Thr Ser Asp Gly Pro Asp Asn Leu Thr Ser Ala Gly Ser Pro Pro Arg
                85                  90                  95

Thr Gly Ser Ile Ser Tyr Ile Asn Ile Ile Met Pro Ser Val Phe Gly
            100                 105                 110

Thr Ile Cys Leu Leu Gly Ile Ile Gly Asn Ser Thr Val Ile Phe Ala
        115                 120                 125

Val Val Lys Lys Ser Lys Leu His Trp Cys Asn Asn Val Pro Asp Ile
    130                 135                 140

Phe Ile Ile Asn Leu Ser Val Val Asp Leu Leu Phe Leu Leu Gly Met
145                 150                 155                 160

Pro Phe Met Ile His Gln Leu Met Gly Asn Gly Val Trp His Phe Gly
                165                 170                 175

Glu Thr Met Cys Thr Leu Ile Thr Ala Met Asp Ala Asn Ser Gln Phe
            180                 185                 190

Thr Ser Thr Tyr Ile Leu Thr Ala Met Ala Ile Asp Arg Tyr Leu Ala
        195                 200                 205

Thr Val His Pro Ile Ser Ser Thr Lys Phe Arg Lys Pro Ser Val Ala
    210                 215                 220

Thr Leu Val Ile Cys Leu Leu Trp Ala Leu Ser Phe Ile Ser Ile Thr
225                 230                 235                 240
```

Pro Val Trp Leu Tyr Ala Arg Leu Ile Pro Phe Pro Gly Gly Ala Val
                245                 250                 255

Gly Cys Gly Ile Arg Leu Pro Asn Pro Asp Thr Asp Leu Tyr Trp Phe
            260                 265                 270

Thr Leu Tyr Gln Phe Phe Leu Ala Phe Ala Leu Pro Phe Val Val Ile
        275                 280                 285

Thr Ala Ala Tyr Val Arg Ile Leu Gln Arg Met Thr Ser Ser Val Ala
    290                 295                 300

Pro Ala Ser Gln Arg Ser Ile Arg Leu Arg Thr Lys Arg Val Thr Arg
305                 310                 315                 320

Thr Ala Ile Ala Ile Cys Leu Val Phe Phe Val Cys Trp Ala Pro Tyr
                325                 330                 335

Tyr Val Leu Gln Leu Thr Gln Leu Ser Ile Ser Arg Pro Thr Leu Thr
            340                 345                 350

Phe Val Tyr Leu Tyr Asn Ala Ala Ile Ser Leu Gly Tyr Ala Asn Ser
        355                 360                 365

Cys Leu Asn Pro Phe Val Tyr Ile Val Leu Cys Glu Thr Phe Arg Lys
    370                 375                 380

Arg Leu Val Leu Ser Val Lys Pro Ala Ala Gln Gly Gln Leu Arg Ala
385                 390                 395                 400

Val Ser Asn Ala Gln Thr Ala Asp Glu Glu Arg Thr Glu Ser Lys Gly
                405                 410                 415

Thr

<210> SEQ ID NO 5
<211> LENGTH: 1269
<212> TYPE: DNA
<213> ORGANISM: Human

<400> SEQUENCE: 5

```
atgtcagtgg gagccatgaa gaagggagtg gggagggcag ttgggcttgg aggcggcagc      60
ggctgccagg ctacggagga agacccccctt cccaactgcg ggcttgcgc tccgggacaa     120
ggtggcaggc gctggaggct gccgcagcct gcgtgggtgg aggggagctc agctcggttg     180
tgggagcagg cgaccggcac tggctggatg gacctggaag cctcgctgct gcccactggt     240
cccaacgcca gcaacacctc tgatggcccc gataacctca cttcggcagg atcacctcct     300
cgcacgggga gcatctccta catcaacatc atcatgcctt cggtgttcgg caccatctgc     360
ctcctgggca tcatcgggaa ctccacggtc atcttcgcgg tcgtgaagaa gtccaagctg     420
cactggtgca acaacgtccc cgacatcttc atcatcaacc tctcggtagt agatctcctc     480
tttctcctgg gcatgccctt catgatccac cagctcatgg gcaatgggt gtggcacttt     540
ggggagacca tgtgcaccct catcacggcc atggatgcca atagtcagtt caccagcacc     600
tacatcctga ccgccatggc cattgaccgc tacctggcca ctgtccaccc catctcttcc     660
acgaagttcc ggaagccctc tgtggccacc ctggtgatct gcctcctgtg ggccctctcc     720
ttcatcagca tcacccctgt gtggctgtat gccagactca tcccttccc aggaggtgca     780
gtgggctgcg gcatacgcct gcccaaccca gacactgacc tctactggtt caccctgtac     840
cagtttttcc tggcctttgc cctgcctttt gtggtcatca gccgcata cgtgaggatc     900
ctgcagcgca tgacgtcctc agtggccccc gcctcccagc gcagcatccg gctgcggaca     960
aagagggtga cccgcacagc catcgccatc tgtctggtct ctttgtgtg ctgggcaccc    1020
tactatgtgc tacagctgac ccagttgtcc atcagccgcc cgaccctcac ctttgtctac    1080
```

-continued

```
ttatacaatg cggccatcag cttgggctat gccaacagct gcctcaaccc ctttgtgtac    1140
atcgtgctct gtgagacgtt ccgcaaacgc ttggtcctgt cggtgaagcc tgcagcccag    1200
gggcagcttc gcgctgtcag caacgctcag acggctgacg aggagaggac agaaagcaaa    1260
ggcacctga                                                             1269
```

<210> SEQ ID NO 6
<211> LENGTH: 422
<212> TYPE: PRT
<213> ORGANISM: Human

<400> SEQUENCE: 6

```
Met Ser Val Gly Ala Met Lys Lys Gly Val Gly Arg Ala Val Gly Leu
 1               5                  10                  15

Gly Gly Gly Ser Gly Cys Gln Ala Thr Glu Glu Asp Pro Leu Pro Asn
             20                  25                  30

Cys Gly Ala Cys Ala Pro Gly Gln Gly Gly Arg Arg Trp Arg Leu Pro
         35                  40                  45

Gln Pro Ala Trp Val Glu Gly Ser Ser Ala Arg Leu Trp Glu Gln Ala
     50                  55                  60

Thr Gly Thr Gly Trp Met Asp Leu Glu Ala Ser Leu Leu Pro Thr Gly
 65                  70                  75                  80

Pro Asn Ala Ser Asn Thr Ser Asp Gly Pro Asp Asn Leu Thr Ser Ala
                 85                  90                  95

Gly Ser Pro Pro Arg Thr Gly Ser Ile Ser Tyr Ile Asn Ile Ile Met
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285

Pro Phe Val Val Ile Thr Ala Ala Tyr Val Arg Ile Leu Gln Arg Met
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335
```

-continued

```
Cys Trp Ala Pro Tyr Tyr Val Leu Gln Leu Thr Gln Leu Ser Ile Ser
                340                 345                 350
Arg Pro Thr Leu Thr Phe Val Tyr Leu Tyr Asn Ala Ala Ile Ser Leu
            355                 360                 365
Gly Tyr Ala Asn Ser Cys Leu Asn Pro Phe Val Tyr Ile Val Leu Cys
    370                 375                 380
Glu Thr Phe Arg Lys Arg Leu Val Leu Ser Val Lys Pro Ala Ala Gln
385                 390                 395                 400
Gly Gln Leu Arg Ala Val Ser Asn Ala Gln Thr Ala Asp Glu Glu Arg
                405                 410                 415
Thr Glu Ser Lys Gly Thr
                420

<210> SEQ ID NO 7
<211> LENGTH: 207
<212> TYPE: DNA
<213> ORGANISM: Human

<400> SEQUENCE: 7
atgtcagtgg gagccatgaa gaagggagtg gggagggcag ttgggcttgg aggcggcagc      60
ggctgccagg ctacggagga agacccccctt cccaactgcg gggcttgcgc tccgggacaa    120
ggtggcaggc gctggaggct gccgcagcct gcgtgggtgg aggggagctc agctcggttg    180
tgggagcagg cgaccggcac tggctgg                                         207

<210> SEQ ID NO 8
<211> LENGTH: 69
<212> TYPE: PRT
<213> ORGANISM: Human

<400> SEQUENCE: 8

Met Ser Val Gly Ala Met Lys Lys Gly Val Gly Arg Ala Val Gly Leu
1               5                   10                  15
Gly Gly Gly Ser Gly Cys Gln Ala Thr Glu Glu Asp Pro Leu Pro Asn
                20                  25                  30
Cys Gly Ala Cys Ala Pro Gly Gln Gly Gly Arg Arg Trp Arg Leu Pro
            35                  40                  45
Gln Pro Ala Trp Val Glu Gly Ser Ser Ala Arg Leu Trp Glu Gln Ala
        50                  55                  60
Thr Gly Thr Gly Trp
65

<210> SEQ ID NO 9
<211> LENGTH: 2483
<212> TYPE: DNA
<213> ORGANISM: Human

<400> SEQUENCE: 9
atgtcagtgg gagccatgaa gaagggagtg gggagggcag ttgggcttgg aggcggcagc      60
ggctgccagg ctacggagga agacccccctt cccaactgcg gggcttgcgc tccgggacaa    120
ggtggcaggc gctggaggct gccgcagcct gcgtgggtgg aggggagctc agctcggttg    180
tgggagcagg cgaccggcac tggctggatg acctggaag cctcgctgct gcccactggt     240
cccaacgcca gcaacaccctc tgatggcccc gataacctca cttcggcagg tgagttgact    300
gggagccctc cctcctctgg gctgtgggtg gaaaatggga aggtttcacc cctgagccaa     360
actgcttggg aaactttatc acagttcttg gggacaagat ctgtggtctg ctttgctctg     420
```

-continued

```
agggycagga gaaaaggggg caatggtccg caggggcaga cgggcaggag cagagcaggg    480
ggcgaaggca tattcagaat ggcaaggaag gggggccagc cgtgagacag caggggaagg    540
ctcgctgctg ggttccaaag atgcttggca gaaaaaattc caggctggaa aagcaagcga    600
gagaagctgg agggtggtat gtgggagaca gctgggggct cactcctgca ctgttagcct    660
cagcttttta ctcccacttg gatgatgagg tctgagacat ccttactgcc acctgggaga    720
ggccctggga agggaagact tcacagagcc atgagggat taacttttct ggtgaattaa    780
gcttcctgac atttccagag ctgcggtgcc ctgggattcc agctttgaag gagaaaggaa    840
ggaaggaaaa gaggaaaggc ttatgtagat aatttttcca ggctgctgag ctccaacaga    900
cagtttctgt ctctgcttca ctcaagaagc ccaggctcag aagataccaa tcaaggaaat    960
ccccgctagg aagcctgggg tagggagagc tgctggcttg accagggcac agccggcaaa    1020
agcctctaca agacagtcac ccacagatat gcccaagaat cagtacacag tttccaacca    1080
gagatctcca aaatgaaaca ctcagggcta cataggaa aagcacgcac acacacac    1140
acacacatac acagacactt acttttgtgt ccttctggct atgctgacga gttttcctgg    1200
tgaagcccgg ggctcacaga gtaatctctg cagacaactg tggttcttgc ctctggtgcc    1260
tgcaggaggc aggcatgttg tgtccttcca agacagatgg ctcagggcac tctggtagga    1320
ttcaccagga aactcatgga gaagggaaaa gggacaagat tagcaacagt gaagggaggg    1380
agaatggtgg gagaggattc cagatgaacg gtgggtcgct ggaggctgag catgccagca    1440
ggatgtcagt tctcagagca aagcccatgt caaacagcca acgcttgctc cttctgtccc    1500
caggatcacc tcctcgcacg gggagcatct cctacatcaa catcatcatg ccttcggtgt    1560
tcggcaccat ctgcctcctg gcatcatcg ggaactccac ggtcatcttc gcggtcgtga    1620
agaagtccaa gctgcactgg tgcaacaacg tccccgacat cttcatcatc aacctctcgg    1680
tagtagatct cctcttttct ctgggcatgc ccttcatgat ccaccagctc atgggcaatg    1740
gggtgtggca cttgggag accatgtgca ccctcatcac ggccatggat gccaatagtc    1800
agttcaccag cacctacatc ctgaccgcca tggccattga ccgctacctg gccactgtcc    1860
accccatctc ttccacgaag ttccggaagc cctctgtggc caccctggtg atctgcctcc    1920
tgtgggccct ctccttcatc agcatcaccc ctgtgtggct gtatgccaga ctcatcccct    1980
tcccaggagg tgcagtgggc tgcggcatac gcctgcccaa cccagacact gacctctact    2040
ggttcacccc gtaccagttt ttcctggcct ttgccctgcc ttttgtggtc atcacagccg    2100
catacgtgag gatcctgcag cgcatgacgt cctcagtggc ccccgcctcc cagcgcagca    2160
tccggctgcg gacaaagagg gtgacccgca cagccatcgc catctgtctg gtcttctttg    2220
tgtgctgggc accctactat gtgctacagc tgacccagtt gtccatcagc cgccgaccc    2280
tcaccttgtgt ctacttatac aatgcggcca tcagcttggg ctatgccaac agctgcctca    2340
accccttttgt gtacatcgtg ctctgtgaga cgttccgcaa acgcttggtc ctgtcggtga    2400
agcctgcagc ccaggggcag cttcgcgctg tcagcaacgc tcagacggct gacgaggaga    2460
ggacagaaag caaaggcacc tga                                              2483
```

<210> SEQ ID NO 10
<211> LENGTH: 12
<212> TYPE: DNA
<213> ORGANISM: Human
<220> FEATURE:
<221> NAME/KEY: misc_feature
<222> LOCATION: (1)...(12)

```
<223> OTHER INFORMATION: r = A or G

<400> SEQUENCE: 10
gccgccrcca tc                                                                 12
```